United States Patent [19]

Asayama et al.

[11] Patent Number: 4,601,793
[45] Date of Patent: Jul. 22, 1986

[54] SENSING AIR-TO-FUEL RATIO FOR ENGINE

[75] Inventors: Yoshiaki Asayama, Himeji; Seiya Kominami, Takasago, both of Japan

[73] Assignees: NGK Spark Plug Co., Ltd.; Mitsubishi Denki Kabushiki Kaisha, both of Japan

[21] Appl. No.: 770,654

[22] Filed: Aug. 28, 1985

Related U.S. Application Data

[62] Division of Ser. No. 606,910, May 4, 1984.

[30] Foreign Application Priority Data

May 11, 1983 [JP] Japan .................................. 58-83588

[51] Int. Cl.$^4$ ............................................. G01N 27/46
[52] U.S. Cl. ..................................... 204/1 T; 204/425; 204/426
[58] Field of Search ......................... 204/1 S, 421–429

[56] References Cited

U.S. PATENT DOCUMENTS

| | | | |
|---|---|---|---|
| 3,654,112 | 4/1972 | Beekmans et al. | 204/1 S |
| 3,691,023 | 9/1972 | Ruka et al. | 204/425 |
| 3,699,032 | 10/1972 | Rapp | 204/1 S |
| 4,272,329 | 6/1981 | Hetrick et al. | 204/425 |
| 4,391,691 | 7/1983 | Linder et al. | 204/425 |
| 4,472,262 | 9/1984 | Kondo et al. | 204/426 |
| 4,505,806 | 3/1985 | Yamada | 204/425 |

*Primary Examiner*—T. Tung
*Attorney, Agent, or Firm*—Leydig, Voit & Mayer, Ltd.

[57] ABSTRACT

This invention can accurately sense not only the stoichiometric air-to-fuel (A/F) ratio but also A/F other than the stoichiometric A/F by altering the electromotive force of an oxygen sensor at a predetermined value during the operation of an engine by using an oxygen concentration measuring device of the solid electrolyte oxygen pumping type.

2 Claims, 3 Drawing Figures

SENSING AIR-TO-FUEL RATIO FOR ENGINE

BACKGROUND OF THE INVENTION

This invention is a divisional application of U.S. Ser. No. 606,910 filed May 4, 1984.

The present invention relates to a device for sensing an air-to-fuel (A/F) ratio by measuring oxygen concentration in exhaust gases for an internal combustion engine, and more particularly to improvements in A/F ratio sensor of oxygen pumping type with ionically conducting solid electrolyte.

It is heretofore well known to control, for example, an engine of a vehicle to operate by stoichiometric air-to-fuel ratio by sensing the combustion state of fuel at the stoichiometric air-to-fuel (A/F) ratio by means of variations of an electromotive force produced due to the difference between the partial pressure of the oxygen of exhaust gas and the partial pressure of the oxygen of air with an oxygen sensor composed of ionically conducting solid electrolyte (e.g., stabilized zirconia). This oxygen sensor can produce a large variation output when the A/F of the ratio of air to fuel by weight is 14.7 of stoichiometric A/F, but produces almost no variation output in other operating air-to-fuel ratios. In case that the engine is operated at an air-to-fuel ratio other than the stoichiometric A/F, the output of the above oxygen sensor could not be utilized.

An oxygen concentration measuring device of the solid electrolyte oxygen pumping type has been proposed for enabling the sensing of air-to-fuel ratios in a wide range as disclosed in U.S. Pat. No. 4,272,329 (Japanese Patent application Laid-open No. 130649/1981). However, this device cannot accurately sense the stoichiometric A/F.

SUMMARY OF THE INVENTION

An object of the present invention is to provide an air-to-fuel ratio sensor for an engine which is capable of accurately sensing the stoichiometric air-to-fuel ratio and of also sensing an air-to-fuel ratio in a range other than the stoichiometric air-to-fuel ratio.

According to the present invention, there is provided an air-to-fuel ratio sensor for an engine which comprises a solid electrolyte oxygen pump for controlling the partial pressure of oxygen in an air gap for introducing exhaust gas of the engine, a solid electrolyte oxygen sensor for generating an electromotive force corresponding to the partial pressure of the oxygen in the air gap and the partial pressure of the oxygen in the exhaust gas other than the air gap, means for controlling the current of the oxygen pump to hold the electromotive force produced by the oxygen sernsor at a predetermined value, and means for altering the electromotive force of the oxygen sensor held at the predetermined value during the operation of the engine.

DETAILED DESCRIPTION OF THE PREFERRED EMBODIMENT

Figure 1:
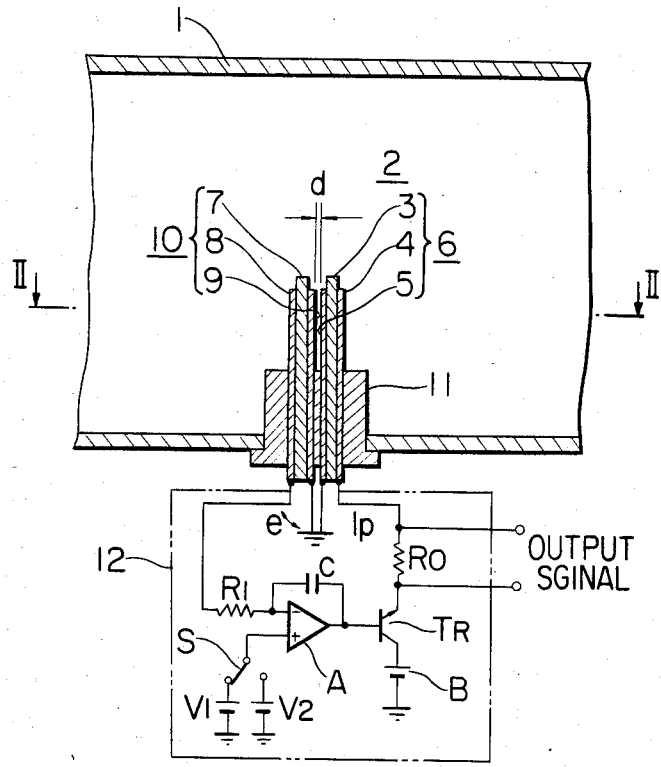
FIG. 1 is a structural view showing an embodiment of an air-to-fuel ratio sensor according to the present invention.
Figure 2:
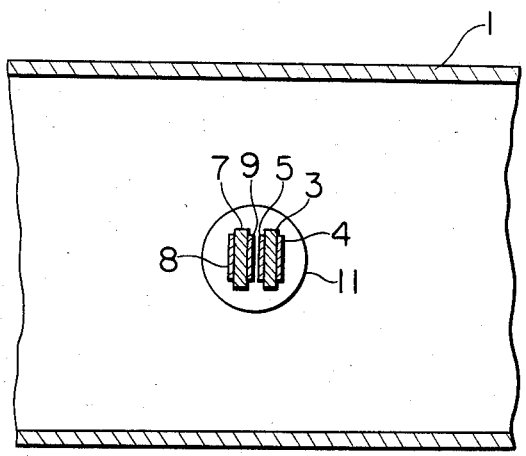
FIG. 2 is a sectional view of the sensor along the line II—II in FIG. 1.

Referring now to the drawings, reference numeral 1 designates an exhaust manifold of an engine, and reference numeral 2 designates an air-to-fuel (hereinafter referred to as A/F) ratio sensor arranged in the exhaust manifold 1. The A/F sensor 2 comprises a solid electrolyte oxygen pump 6 composed by providing platinum electrodes 4 and 5 on both side surfaces of an inonically conducting solid electrolyte (stabilized zirconia) 3, formed in the shape of a flat plate having a thickness of approx. 0.5 mm, a solid electrolyte oxygen sensor 10 composed by providing platinum electrodes 8 and 9 on both side surfaces of ionically conducting solid electrolyte 7 formed in the shape of a flat plate and constructed in the same manner as the oxygen pump 6, and a supporting base 11 for oppositely disposing the oxygen pump 6 and the oxygen sensor 10 at a small gap d of approx. 0.1 mm therebetween. Reference numeral 12 depicts an electronic control device which serves the functions of: applying an electromotive force e produced between the electrodes 8 and 9 of the oxygen sensor 10 through a resistor $R_1$ to the inverting input terminal of an operational amplifier A; driving a transistor $T_R$ by the output of the operational amplifier A by a value proportional to the difference between the electromotive force e and a reference voltage $V_1$ applied to the non-inverting input terminal of the operational amplifier A; and controlling a pump current $I_P$ flowing between the electrodes 4 and 5 of the oxygen pump 6. More specifically, the electronic control device 12 serves to supply the pump current $I_P$ necessary to maintain the electromotive force e at a constant value ($V_1$). The electronic control device 12 further includes a resistor $R_0$ for producing an output signal corresponding to the pump current $I_P$ supplied from a D.C. power source B of a pump current supplying means. This resistor $R_0$ is selected to be a predetermined resistance value so that the pump current $I_P$ may not flow excessively corresponding to the D.C. power source B. Reference character C designates a condenser, and reference character S depicts a switch for switching the reference voltage from $V_1$ to $V_2$.

Figure 3:
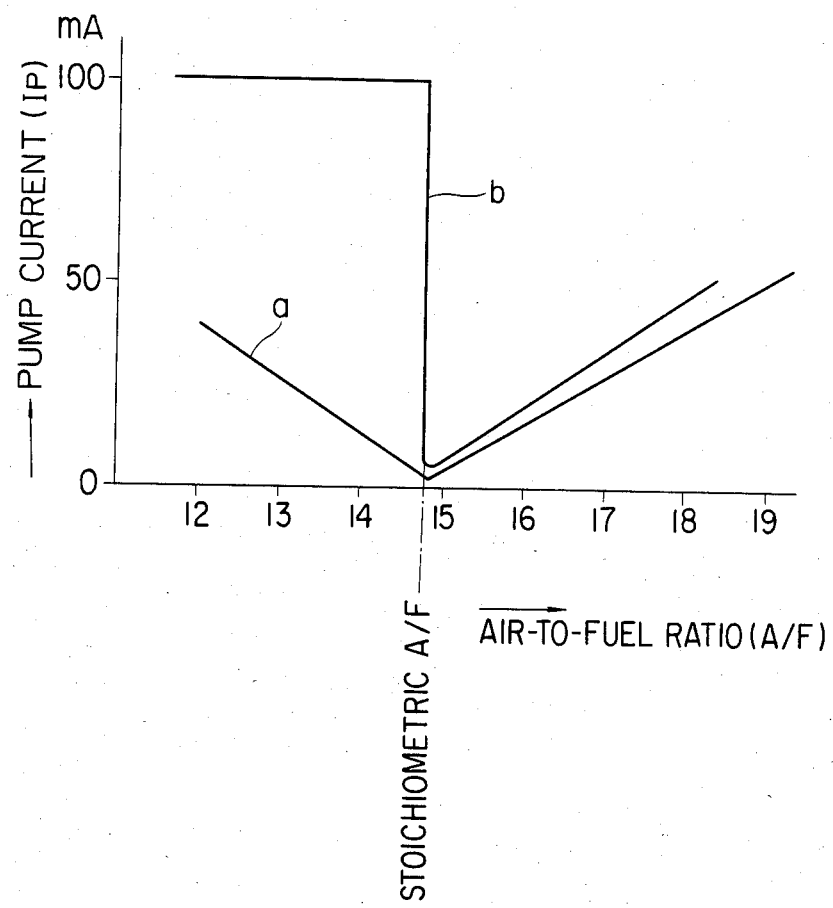
FIG. 3 is a graphical diagram of the sensor of the invention.

The results of tests conducted with the A/F sensor of the present invention thus constructed and mounted in a gasoline engine having a 2000 cc displacement used in a Japanese automobile are shown in FIG. 3. When an excess pump current $I_P$ caused to flow, the oxygen pump 6 is damaged. Accordingly, the pump current $I_P$ was limited by the D.C. power source B so as not to allow a current of 100 mA or higher to flow. As a result of tests conducted by setting the first reference voltage $V_1$ to 55 mV and the second reference voltage $V_2$ to 200 mV, when the reference voltage was set to $V_1 = 55$ mV by the switch S, the characteristic curve (a) shown in FIG. 3 was obtained. When the reference voltage was altered to $V_2 = 200$ mV by the switch S, the characteristic curve (b) shown in FIG. 3 was obtained. Since two air-to-fuel ratio points of the same pump current value existed in the curve (a) when the A/F was sensed in a wide range of 12 to 19 by utilizing the above-described characteristics, the A/F could not be sensed only by the pump current value. Since the pump current $I_P$ did not vary in the range lower than the stoichiometric A/F, 14.7 though the A/F could be sensed in the range of the stoichometric A/F, 14.7 and above the stoichiometric A/F in the characteristic curve (b) in FIG. 3, the A/F could not be sensed in this range. Therefore, in the invention, the reference voltage is arbitrarily altered to $V_1$ or $V_2$ by the switch S so as to sense the A/F in the wide range as described above by utilizing the both characteristic curves (a) and (b) in FIG. 3. For instance, when the A/F during the operation of the engine is sensed, the reference voltage is first set by the switch S to $V_2$. Then, when the A/F during operation of the engine is lower than the stoichiometric A/F, the pump current $I_P$ becomes 100 mA by the characteristic curve (b) in FIG. 3, while when the A/F is higher than the stoichiometric A/F, the pump current $I_P$ becomes lower than 100 mA. Consequently, it can be sensed whether the A/F during the operation of the engine is lower or higher than the stoichiometric A/F. When the pump current abruptly decreases from 100 mA, the fact that the A/F during the operation of the engine is the stoichiometric A/F can be sensed. Thus, the reference voltage is altered by the switch S to $V_1$, the A/F during the operation of the engine can be sensed in the range lower than or higher than the stoichiometric A/F by the characteristic curve (a) in FIG. 3. In the above description, the first reference voltage $V_1$ is set to 55 mV and the second reference voltage $V_2$ is set to 200 mV. However, sufficient effect can be obtained in practice when $V_1$ is set to a predetermined value in the range of 20 to 70 mV and $V_2$ is set to a predetermined value in the range of 150 to 500 mV.

As shown by the characteristic curves in FIG. 3, the reasons why the pump current $I_P$ alters proportionally to the A/F in the range where the A/F is larger than the stoichiometric A/F as described above are as follows. The partial pressure of oxygen in the exhaust gas introduced into the small gap d is altered by the operation of the oxygen pump 6, the partial pressure of the oxygen is thereby differentiated from the partial pressure of the oxygen of the exhaust gas flowing in the exhaust manifold 1, and when the pump current $I_P$ supplied to the oxygen pump 6 is controlled so that the electromotive force e of the oxygen sensor 10 generated in response to the difference between the partial pressure of the oxygen of the exhaust gas thus introduced into the small gap and the partial pressure of the oxygen of the exhaust gas flowing in the exhaust manifold 1 may become a predetermined value, and, accordingly, the control of the dispersion of the oxygen gas is carried out over a wide range by measuring the gas in the small gap d. Then, the pump current $I_P$ alters proportional to the oxygen concentration in the exhaust gas. Since the A/F is substantially proportional to the oxygen concentration, the pump current $I_P$ resultantly varies proportional to the A/F. The reason why the pump current $I_P$ alters in the range smaller than the stoichiometric A/F is considered that the A/F sensor 2 senses the carbon monoxide (CO) concentration in the exhaust gas.

What is claimed is:

1. A method of determining the air-to-fuel ratio A/F of an engine using a sensor unit mounted in the exhaust gas passage of the engine having a sensor and an oxygen pump separated by a gap, said oxygen pump comprising a solid electrolyte oxygen pump supplied with current from a source to control the partial pressure of oxygen in the gap, said sensor comprising a solid electrolyte oxygen sensor for producing electromotive force corresponding to the difference between the partial pressure of the oxygen in the gap and the partial pressure of the oxygen in the exhaust gas flowing through the passage outside of the gap, said method comprising the steps of:

introducing exhaust gas from the passage into the gap;

controlling the current Ip to said oxygen pump so as to maintain the electromotive force produced by said oxygen sensor at a first constant predetermined value higher than about 150 mV whereby the variation in the magnitude of the pump current Ip as a function of the air-to-fuel ratio A/F is increased in the vicinity of the stoichiometric A/F substantially in the manner represented by the characteristic curve b in FIG. 3;

altering the electromotive force produced by said oxygen sensor from said first constant predetermined value to a second constant predetermined value in the range of 20 mV to 70 mV whereby the variation in the magnitude of the pump current Ip as a function of the air-to-fuel ratio A/F is substantially linear in both the lean and rich ranges in the manner represented by the characteristic curve a in FIG. 3; and producing an output signal corresponding to the pump current Ip to said oxygen pump for sensing the air-to-fuel ratio A/F of the engine as said A/F ratio varies according to one of the different characteristic curves a and b corresponding to one of said first and second constant values of electromotive force.

2. A method according to claim 1 wherein said first constant predetermined value is in the range of about 150 mV to 500 mV.

* * * * *